United States Patent
Watanabe et al.

[11] Patent Number: 6,104,940
[45] Date of Patent: Aug. 15, 2000

[54] ELECTRODE PROBE AND BODY FLUID EXAMINATION EQUIPMENT INCLUDING THE SAME

[75] Inventors: Motokazu Watanabe, Kadoma; Shin Ikeda, Katano; Toshihiko Yoshioka; Shiro Nankai, both of Hirakata, all of Japan

[73] Assignee: Matsushita Electric Industrial Co., Ltd., Osaka-fu, Japan

[21] Appl. No.: 09/326,350

[22] Filed: Jun. 4, 1999

[30] Foreign Application Priority Data

Jun. 11, 1998 [JP] Japan .................................. 10-163391

[51] Int. Cl.[7] ....................................................... A61B 5/05
[52] U.S. Cl. ........................... 600/345; 600/347; 600/365; 600/372; 600/573; 600/584
[58] Field of Search ...................... 600/345–347, 600/363, 365, 372, 382, 573, 584; 606/41–52; 204/403, 411–412; 435/287.1, 287.9

[56] References Cited

U.S. PATENT DOCUMENTS

| | | |
|---|---|---|
| 4,545,382 | 10/1985 | Higgins et al. . |
| 4,812,210 | 3/1989 | Bonivert et al. .................... 204/434 X |
| 5,243,516 | 9/1993 | White . |
| 5,542,945 | 8/1996 | Fritzsch .................................. 606/50 X |
| 5,628,890 | 5/1997 | Carter et al. ......................... 204/403 X |

FOREIGN PATENT DOCUMENTS 0 351 891 A2   1/1990   European Pat. Off. .

*Primary Examiner*—Cary O'Connor
*Assistant Examiner*—Ryan Carter
*Attorney, Agent, or Firm*—Akin, Gump, Strauss, Hauer & Feld, L.L.P.

[57] ABSTRACT

Disclosed is an electrode probe and a body fluid examination equipment enabling examination of a trace amount of body fluid. The electrode probe comprises an insulating needle member, a working electrode lead disposed in the needle member, a working electrode whose lead is protruding outside from the needle member, a counter electrode disposed on the surface of the needle member, a lead connected to the counter electrode, and a reagent layer disposed in contact with or in the vicinity of the working and counter electrodes of the electrode system. When a trace amount of body fluid leaking on the skin surface is brought into contact with the reagent layer, the reagent layer dissolves which results in electron transfer whereby information about the concentration of analyte in the body fluid can be obtained from the electrode system.

21 Claims, 6 Drawing Sheets

FIG.2A
FIG.2B
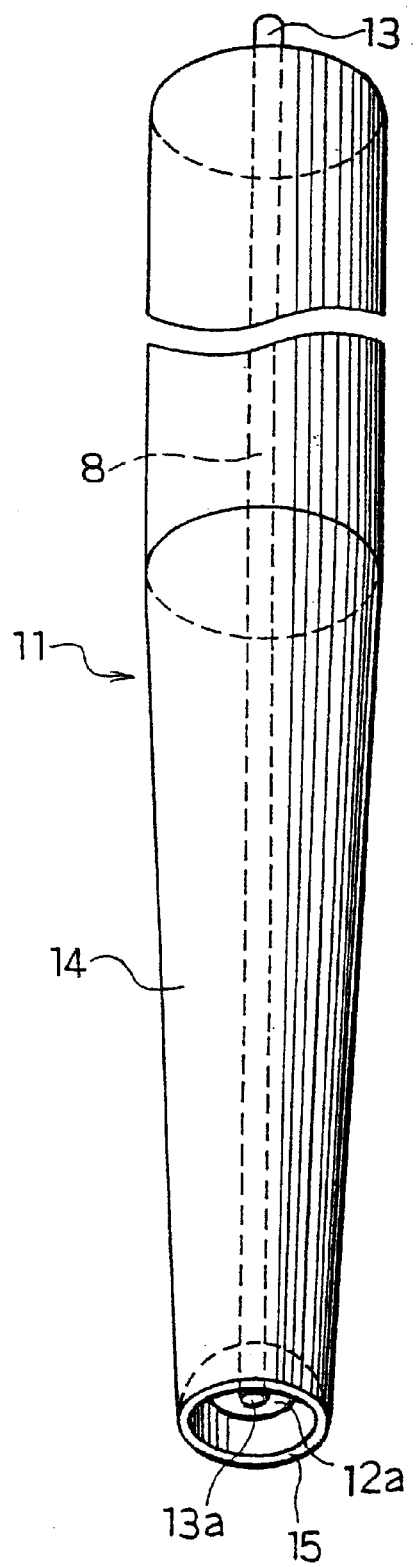
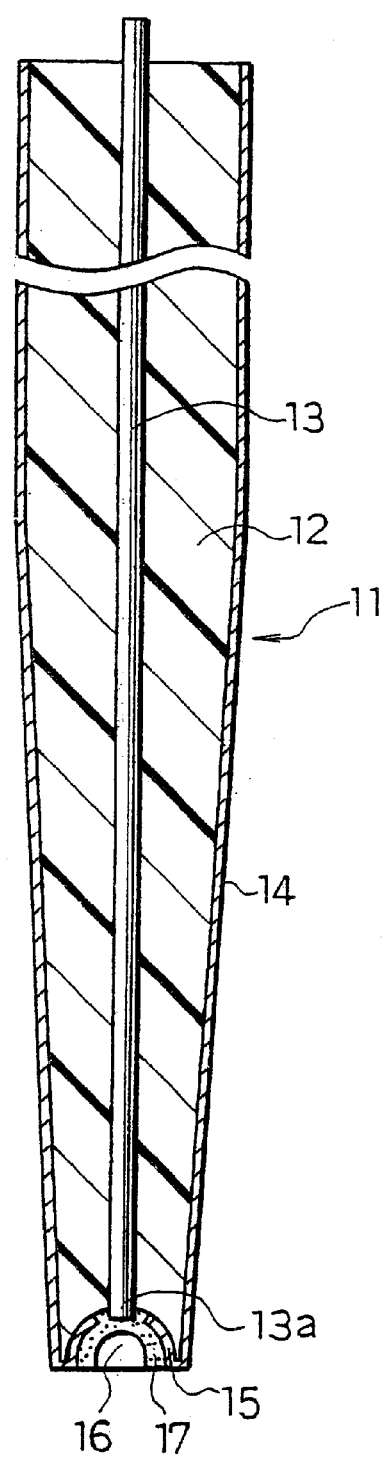

ELECTRODE PROBE AND BODY FLUID EXAMINATION EQUIPMENT INCLUDING THE SAME

BACKGROUND OF THE INVENTION

The present invention relates to an electrode probe for measuring the concentration of analyte contained in a trace amount of body fluid and a body fluid examination equipment for measuring the concentration of analyte contained in body fluids leaking on the skin surface.

Normally, patients with diabetes are forced to measure their sugar blood level 3 to 7 times a day for controlling their blood sugar level. At measurement, although small in amount, bleeding from the finger or the like which accompanies pain is inevitable. Therefore, a measurement method of blood sugar level with less pain has been desired.

Conventionally known method for measuring blood sugar level damages the skin using a body fluid leaking instrument, for example, lancet, supplies the leaking blood from the damaged site to a recess formed on a sensor strip, and obtains information on the blood sugar output from 2 electrodes disposed in the recess (see Japanese Laid-Open Patent Publication No. Hei 9-2651278, for example).

However, any commercially available sensor strip for measuring blood sugar has a problem that it normally requires 3 $\mu$l to 10 $\mu$l blood. If blood sugar can be measured with less than 3 $\mu$l blood, the damage made on the skin for sampling blood can be more superficial than the current level thereby reducing the pain associated with bleeding.

BRIEF SUMMARY OF THE INVENTION

The object of the present invention is therefore to provide an electrode probe and a body fluid examination equipment enabling blood examination even with a trace amount of blood.

In order to solve the above-mentioned problem, the present invention provides an electrode probe comprising an insulating needle member, an electrode system including a counter electrode and a working electrode disposed on the surface of the needle member, a lead connected to the counter electrode and a lead connected to the working electrode.

In a preferred mode of the present invention, a linear conductive member which is finer than the needle member is embedded in the needle member such that its tip end protrudes from the tip end of the needle member in order to use the protruding portion as a working electrode.

In another preferred mode of the present invention, a reagent layer is disposed in contact with or in the vicinity of the electrode system.

In still another preferred mode of the present invention, the insulating needle member has a pit at its tip end in order to dispose therein an electrode system including a counter electrode and a working electrode.

It is also preferable to dispose the reagent layer in the pit.

In still another preferred mode of the present invention, the electrode probe may further comprise a third electrode and a lead connected thereto.

The present invention provides a body fluid examination equipment using the electrode probe as noted above, comprising means for applying a voltage across the electrode system of the electrode probe and obtaining analyte information from the electrode system in the form of electric signal, means for determining the measurement value of an analyte based on the electric signal, and a body fluid leaking instrument.

The equipment preferably further comprises display means for displaying the measurement value as determined.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 2A illustrates an external view of an electrode probe in accordance with another example of the present invention.

FIG. 2B illustrates a longitudinal cross-sectional view of the biosensor of FIG. 2A.

DETAILED DESCRIPTION OF THE INVENTION

Figures 1A, 1B:
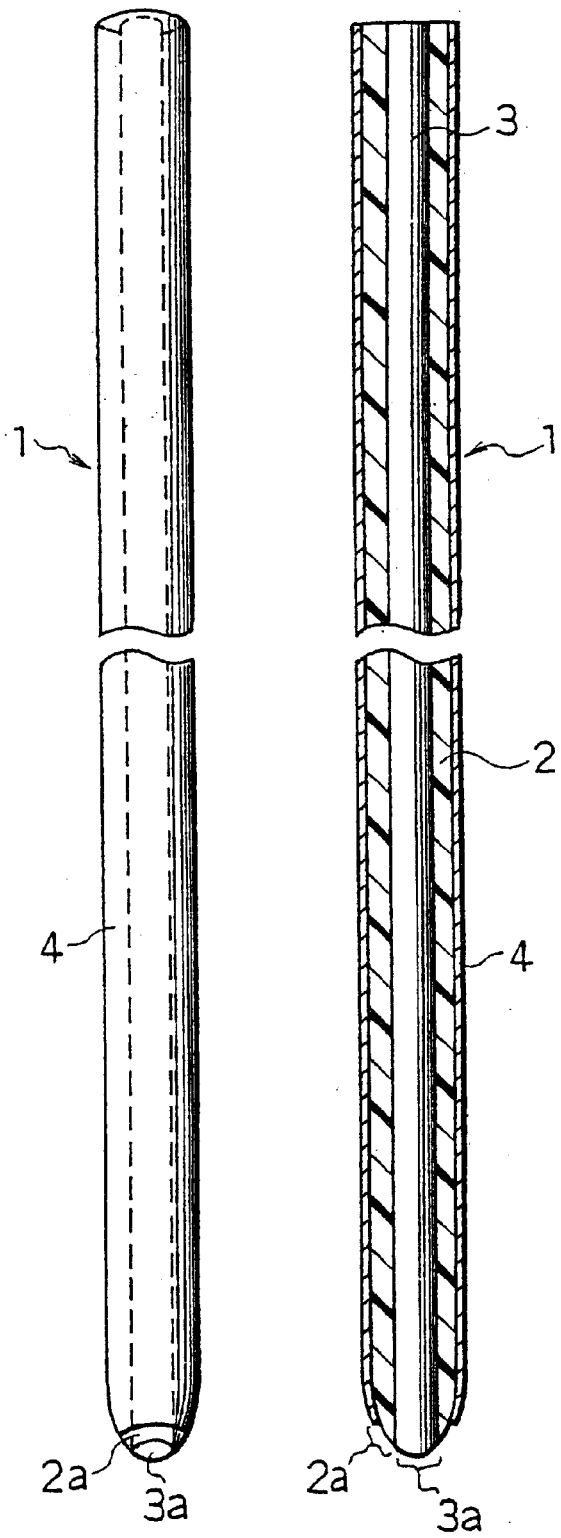
FIG. 1A illustrates an external view of an electrode probe in accordance with one example of the present invention.
FIG. 1B illustrates a longitudinal cross-sectional view of the biosensor of FIG. 1A.

As stated above, the electrode probe in accordance with the present invention has a counter electrode, a working electrode, each disposed on the surface of a needle member, and a reagent layer disposed in contact with or in the vicinity of the electrode system. This structure enables to contact the electrode system with the blood or the like leaking on the skin surface. Particularly, positioning of the electrode system at the tip end of the needle member facilitates contacting the electrode system with the blood or the like on the skin. The structure of the electrode probe where a fine electrode system is disposed on the tip end of the needle member also facilitates measurement of the concentration of analyte in the blood even when the amount of blood sample leaking on the skin surface is extremely small.

The structure where a conductive member is protruding from the tip end of an insulating needle member, which protruding portion is used as a working electrode, readily yields a needle electrode with a uniformly regulated electrode area.

The structure where a pit is formed at the tip end of the electrode probe to form therein an electrode system facilitates regulating the amount of blood in the pit uniformly by pressing the pit against the surface of the skin or the like. This structure also facilitates prevention of possible evaporation of water from the blood.

Adjustment of the protruding length of the working electrode from the pit at the tip end of the probe to be shorter than the depth of the pit can eliminate worries about possible breaking of the working electrode by finger or the like.

Furthermore, a provision of a body fluid leaking instrument in the equipment facilitates continuous operations of the process to leak and examine body fluids.

The body fluids examined by the equipment of the present invention include blood, lymph, intercellular fluid, sweat, etc. all of which permit sampling from the skin surface.

In the following, the present invention will be described more specifically referring to the drawings.

EXAMPLE 1

FIG. 1A shows an external view of an electrode probe embodied in the present example and FIG. 1B is the longitudinal cross-sectional view of the electrode probe. Electrode probe 1 of the present invention comprises a needle member 2 made of an insulating material, a working electrode lead 3 made of a conductive material and embedded in the center of the needle member 2 and a counter electrode 4 made of a conductive material which is disposed on the outer surface of the needle member 2 and doubles as a lead. The tip end of the working electrode lead 3 which is exposed and protruding outside the needle member 2 is used as a working electrode 3a. The tip end of the needle member 2 is exposed between the working electrode 3a and the counter electrode 4, which portion functions as an insulating portion 2a.

Next, the method for producing the electrode probe will be described.

First, a needle-shaped die (not shown) is prepared and a linear carbon needle which will form the working electrode and its lead is placed in the die. Subsequently, molten plastic is poured into the die and solidified together with the carbon needle. The needle member thus formed is removed from the die. After masking the portions to be used as the working electrode and the insulating portion, the entire needle member is coated with a thin palladium film by sputtering.

As to the dimensions, the needle member 2 is 50 mm in length and 2 mm in diameter. The carbon needle for the working electrode lead 3 is 0.8 mm in diameter. The distance between the working electrode and the counter electrode which are spaced by the exposed part (i.e., insulating portion 2a) of the needle member is 0.3 mm. The electrode probe 1 shaped like a needle may have a bar-like segment with the same size for the top and bottom as shown in FIG. 1 or may be tapered at the tip end.

In the foregoing example, although carbon was used as the material for forming the working electrode and its lead, platinum, gold, diamond or the like may be used. Alternatively, a nonconductive material with the periphery being coated with a conductive material such as platinum, carbon, etc. may also be used. Similarly, although a thin film formed by sputtering palladium was used as the counter electrode and its lead, the thin film may be formed by vapor depositing palladium. Alternatively, the film may be formed by sputtering or vapor depositing platinum, carbon, gold or something like that in place of palladium. As the insulating material, glass, resin such as polyethylene terephthalate, rubber or something like that may be used in place of plastics.

EXAMPLE 2

FIG. 2A shows an external view of an electrode probe embodied in the present example and FIG. 2B shows the longitudinal cross-sectional view of the electrode probe. Needle member 12 which is made of an insulating material and serves as the base of forming electrode probe 11 is tapered at its lower half so that the tip end has a smallest diameter. The needle member has a pit 16 formed at the tip end. In the center of the needle member 12, a working electrode lead 13 made of a conductive material is embedded such that the tip end thereof protrudes toward the pit 16 of the needle member 12. The protruding portion 13a is used as a working electrode. On the outer surface of the needle member 12, a counter electrode lead 14 made of a conductive material is disposed and a counter electrode 15 is formed in the pit 16 so that it becomes continuous to the counter electrode lead 14 and surrounds the working electrode 13a. In the pit 16, a reagent layer 17 for which a detailed description will be made in Example 3 is disposed. The reagent layer has been omitted from FIG. 2A.

Next, the method for producing the electrode probe of Example 2 will be described.

First, a needle-shaped die having a pit (not shown) is prepared. In the center of the pit of the die, a hole is formed into which a linear carbon needle which will form the working electrode and its lead should be inserted and occluded. At insertion, the carbon needle is arranged so that it would not protrude outside the pit of the forming needle member. Then, molten plastic is poured into the die and solidified together with the carbon needle. In this structure, since the carbon needle has been solidified so as not to protrude outside the pit, there is no worry about possible breaking of the working electrode due to contact with finger or the like during measurement of blood sugar or the like. Then, the needle member thus formed is removed from the die. After masking the working electrode-associated region in the pit 16 and its periphery which portion will be serve as the insulating portion 12a, the pit is covered with palladium by sputtering. Finally, the entire lateral side of the needle member 12 is coated with palladium.

The needle member 12 is 50 mm in length, 4 mm in widest diameter and 2 mm in smallest diameter. The carbon needle is 0.8 mm in diameter. The distance of the insulating portion between the working electrode and the counter electrode is 0.3 mm. In this example, the pit is shaped like a hemisphere. Since a hemisphere of 2 mm diameter has a volume of 2.1 $\mu l$, the electrode probe of this example can cope with 2.1 $\mu l$ of body fluids or more. Key to management of smaller amounts of body fluids than the above is to reduce the volume of the pit. Otherwise, the diameter of the needle member should be reduced.

EXAMPLE 3

Figure 3:
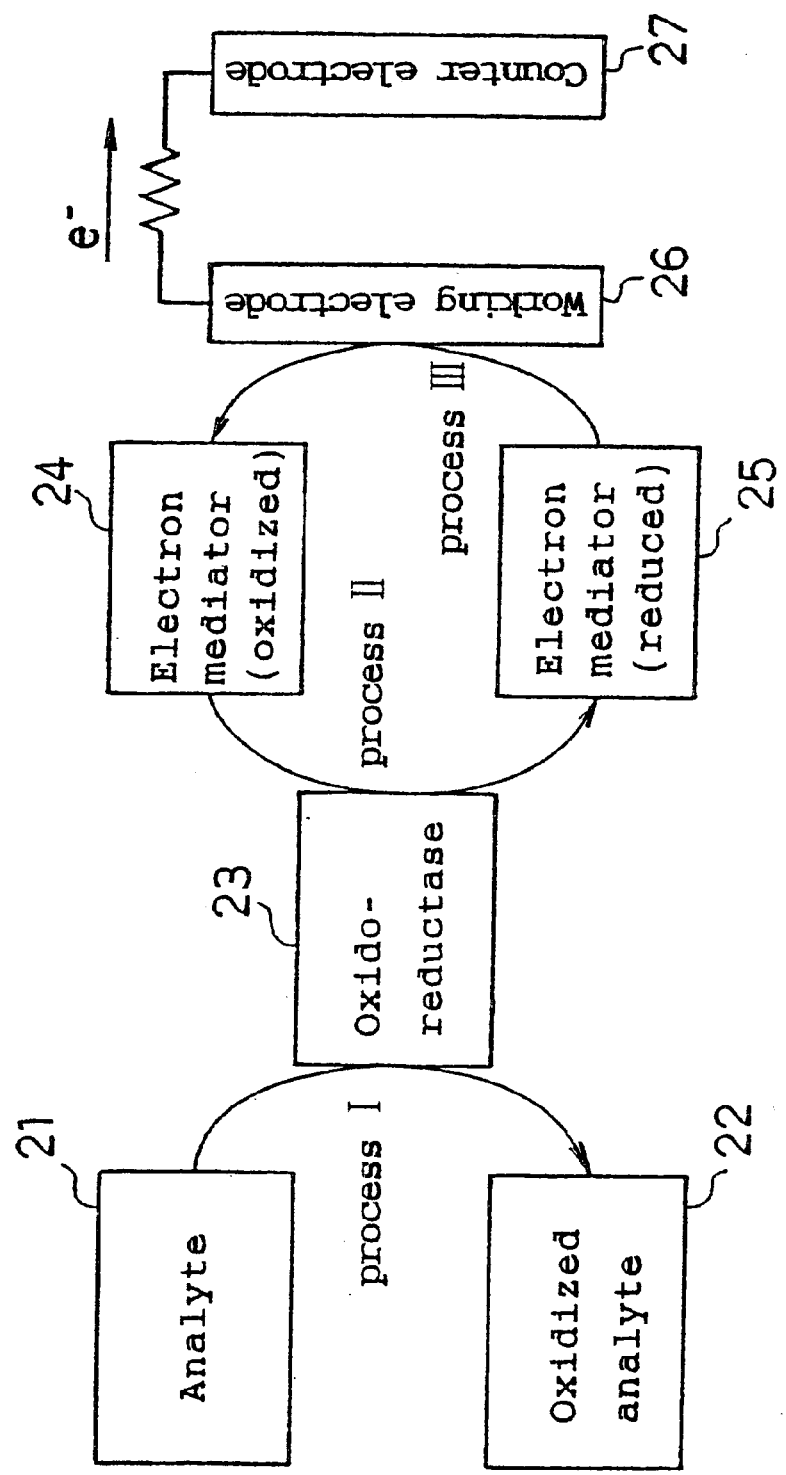
FIG. 3 is a block diagram illustrating the course of reaction occurring during measurement of an analyte.

FIG. 3 is a block diagram showing the course of reaction during measurement of an analyte.

In measuring the concentration of analyte 21, the analyte is oxidized by an oxidoreductase 23 (process I). The oxidation accompanies reduction of an electron mediator 24 (process II). In the next process (process III), the electron mediator is oxidized on the working electrode by applying a voltage across working electrode 26 and counter electrode 27. At that time, the current across the two electrodes is measured. The current value depends on the concentration of reduced form electron mediator 25 whose concentration depends on the concentration of analyte 21. Therefore, the concentration of analyte can be obtained by simple measurement of the current across the working electrode and the counter electrode.

In this example, the method for preparing the reagent layer will be described by taking measurement of blood sugar as an example. Measurement of blood sugar requires two different reagents; an oxidoreductase and an electron mediator. Here, glucose oxidase is the oxidoreductase and potassium ferricyanide is the electron mediator. First, an aqueous solution of glucose oxidase and potassium ferricyanide is prepared. In the aqueous solution, an electrode probe as produced in above Example 1 or Example 2 is immersed at its tip end and removed. Then, the aqueous solution adhering to the tip end of the electrode probe is dried. In this way, the reagent layer is formed. FIG. 2B illustrates the structure of the electrode probe formed with a reagent layer in the pit of the needle member.

Alternatively, the aqueous solution of glucose oxidase and potassium ferricyanide may be sprayed onto the tip end or pit of the needle member and dried.

Otherwise, glutaraldehyde steam may be supplied to the dried reagent layer in order to fix the reagent layer at the tip end or in the pit of the needle member.

In another mode of forming the reagent layer, a conducive material which will form the working electrode and its lead may be mixed with glucose oxidase and potassium ferricyanide prior,to formation of the working electrode and its lead, and after production of the working electrode and its lead, the reagent layer is formed exclusively on the formed working electrode.

Otherwise, a filter, glass filter, gauze or something like that impregnated with a reagent mixture may be fixed onto the tip end of the needle member and dried.

Other electron mediator such as ferricinium ion, parabenzoquinone or the like may be used in place of potassium ferricyanide.

The oxidoreductase may be glucose dehydrogenase or hexose oxidase in place of glucose oxidase. The use of lactate oxidase in place of glucose oxidase will facilitate measurement of blood lactate level and the use of uricase will facilitate measurement of blood uric acid (urate) level. Furthermore, the use of cholesterol oxidase in combination with cholesterol esterase in place of glucose oxidase will facilitate measurement of total cholesterol concentration in the blood.

Next, operation of the electrode probe as shown in FIG. 2A and FIG. 2B will be described. Of the carbon needle 13 penetrating the needle member 12, the protruding portion 13a toward the pit 16 functions as the working electrode. Therefore, if the protruding length of the carbon needle is held constant, the surface area of the working electrode can be regulated at a constant area. Furthermore, the amount of blood in the pit 16 can be kept constant by pressing the pit against the surface of the skin or the like. This structure also facilitates prevention of possible evaporation of water in the blood even when the blood amount is small.

Because of the presence of the reagent layer 17 in the pit 16, supply of a sample solution such as blood into the pit causes dissolution of the reagent layer in the sample solution, which promotes the reaction of the process I and process II as shown in FIG. 3. At that time, of the conductive material doubling as the counter electrode lead 14, the area which can make contact with the blood supplied functions as the counter electrode. Application of a voltage across the working electrode lead 13 and the counter electrode lead 14 after a predetermined time promotes the reaction of the process III and oxidation current flows across the two leads. The current is measured to determine the concentration of analyte.

EXAMPLE 4

Figure 4:
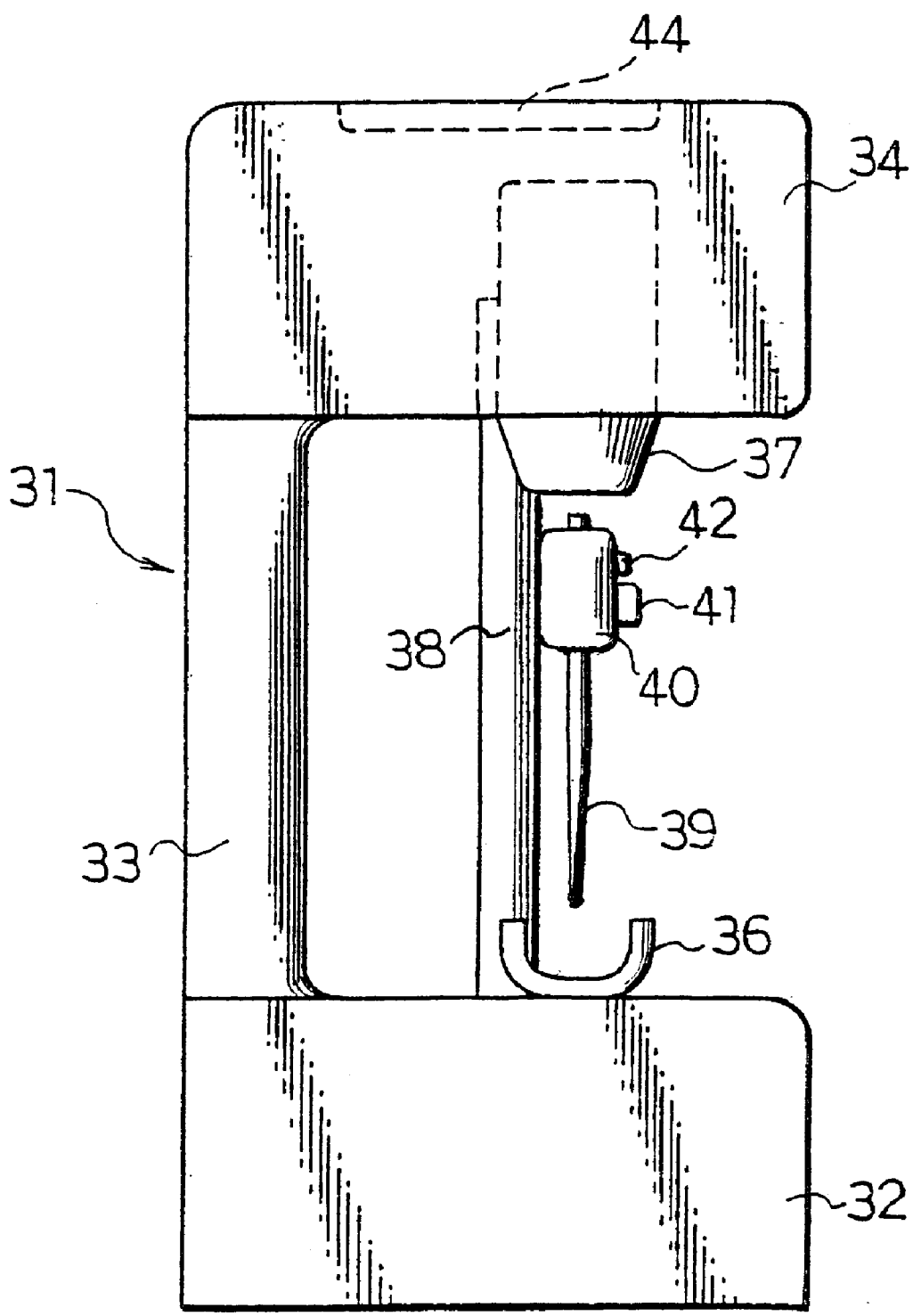
FIG. 4 is a front view illustrating the vital parts of a body fluid examination equipment in accordance with one example of the present invention.
Figure 5:
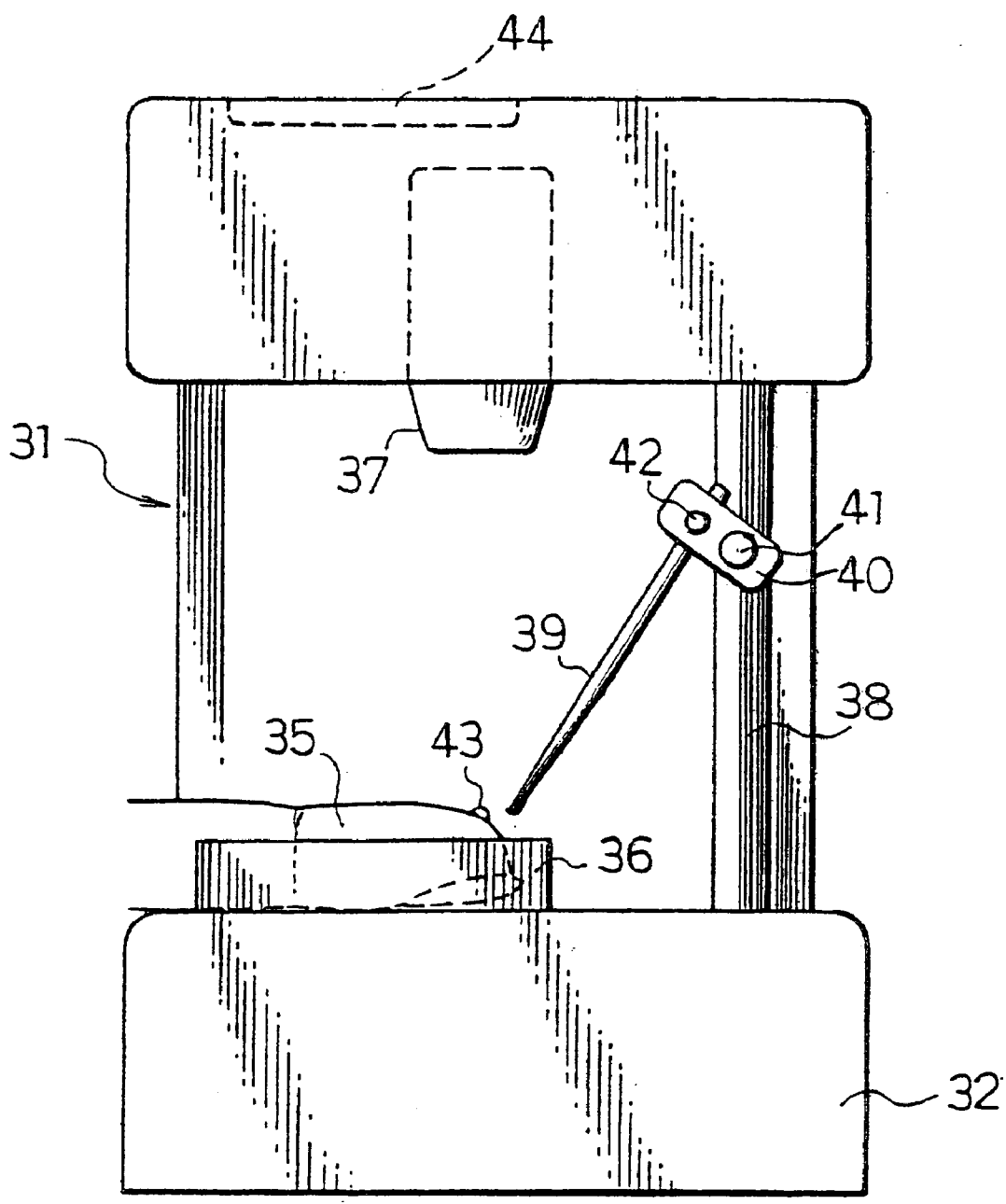
FIG. 5 is a right side view of the equipment.

FIG. 4 illustrates the front view of body fluid examination equipment 31 of Example 4 and FIG. 5 illustrates the right lateral side view of the equipment.

The body fluid examination equipment 31 comprises a base 32 and an upper member 34 which is disposed on the base 32 being supported by a column 33. A guide 36 for resting host's finger 35 is formed on the base 32. On the other hand, laser beam emitting apparatus 37 is disposed on the upper member 34 for emitting laser beam toward the finger 35 on the guide 36 to leak the body fluids. On the upper member 34, display means 44 is disposed for displaying measured value, which value can be read from the upper side of the equipment. On a support 38, a fixer 40 with an electrode probe 39 is mounted by means of a screw 41. The electrode probe 39 having a working electrode, a counter electrode and a reagent layer (each not shown) at the tip end thereof is fixed on the fixer 40 with a screw 42.

Next, operation of the body fluid examination equipment 31 will be described.

First, the host's finger is rested on the guide 36. When the finger tip comes immediately under the laser beam emitting apparatus 37, laser beam is emitted which induces a slight injury of the skin surface from which a trace amount of blood 43 comes out. While keeping the blood to leak, the finger 35 is pushed along the guide 36 and the skin surface is pressed slightly against the electrode probe 39 so that the blood leaking on the skin surface makes contact with the tip end of the electrode probe 39. As a result, the reagent layer (not shown) dissolves in the blood which triggers the oxidation of the analyte. The finger is fixed for a predetermined time in this state. Although not shown, a circuit system applies a voltage across the working and counter electrodes (both not shown) after a predetermined time and inputs information about the analyte into the equipment in the form of electric signal.

In this structure, since the position where laser beam is irradiated on the finger is close to the tip end of the electrode probe, time and effort for transferring the blood on the skin surface to a sensor as required by the prior art can be eliminated. Furthermore, the equipment of the present invention allows a provision of a mechanism which automatically senses contact of the blood with the electrode probe by sensing, for example, liquid junction between the working electrode and the counter electrode due to blood. This structure is useful for the blinds due to diabetes or the like to make measurement of the blood sugar level by themselves because it facilitates determination as to whether the blood makes contact with the tip end of the electrode probe by only sliding the finger along the guide.

In the foregoing example, although a laser beam emitting apparatus was used as the body fluid leaking instrument, other instrument may be used such as puncture means using repulsion of a spring, in order to leak body fluids.

EXAMPLE 5

Figure 6:
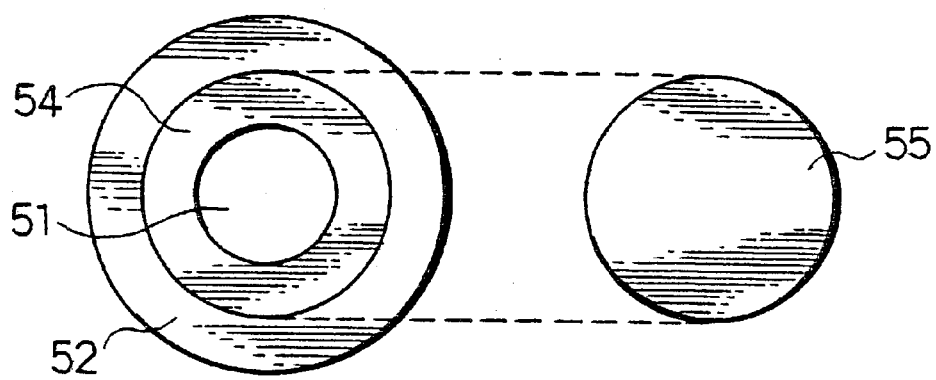
FIG. 6 is a projection of the tip end of an electrode probe and a sketch of the shape of a mask used in forming the electrodes.
Figure 7:
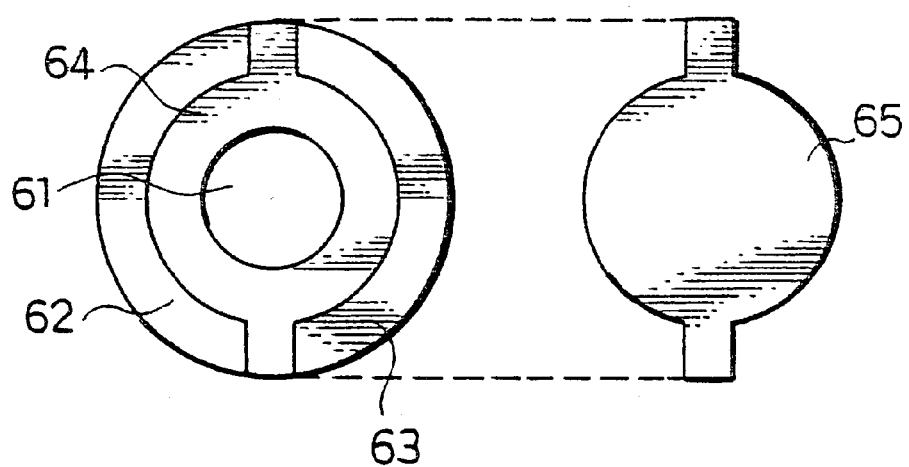
FIG. 7 is a projection of the tip end of another electrode probe and a sketch of the shape of a mask used in forming the electrodes.

FIG. 6 and FIG. 7 show a projection of the tip end of an electrode probe and a sketch of the shape of a mask used during coating the electrode probe with palladium. In FIG. 6, an electrode system formed by a working electrode 51 and a counter electrode 52, and the shape of a mask 55 for masking the electrode system are shown. The area not covered with the mask 55 is coated with palladium and functions as the counter electrode 52. The working electrode and the counter electrode are isolated from each other by the exposed portion of a needle member 54 made of an insulating material. In FIG. 7, on the other hand, an electrode system formed by a working electrode 61, a counter electrode 62 and a third electrode 63 is shown. Numeral 65 shows the shape of a mask 65, which shape is partially different from that of FIG. 6. Coating with palladium or the like yields 2 electrodes except for the working electrode. Of the 2 electrodes, one can serve as the counter electrode 62 and the other as the third electrode 63. The third electrode may function as, for example, reference electrode or liquid junction sensing electrode. The electrodes are isolated from each other by the exposed part of a needle member 64.

The method for producing the third electrode lead uses similar palladium sputtering onto the lateral surface of the needle member to that used in producing the counter electrode lead. At sputtering, the third electrode lead and the counter electrode lead are isolated with a mask during coating the electrode probe with palladium. Alternatively, laser beam may be irradiated onto the formed palladium coating in order to expose the needle member immediately under the formed palladium coating to isolate the third electrode and counter electrode leads. As in Example 1, the material for forming coating may be ones other than palladium and the method for forming coating is not limited to sputtering.

As discussed above, the electrode probe in accordance with the present invention wherein the counter electrode, working electrode and reagent layer are all disposed on the tip end of a needle member facilitates measurement of the concentration of an analyte in an extremely small amount of leaking blood on the skin surface.

Furthermore, a provision of a pit at the tip end of the electrode probe prevents possible evaporation of water in the blood, because the amount of blood in the pit can be regulated at a constant level by pressing the tip end of the probe against the surface of the skin or the like.

A combination of the electrode probe of the present invention with a body liquid leaking instrument facilitates consecutive operations of the process to leak and examine blood or the like.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. An electrode probe comprising an insulating needle member, an electrode system including a counter electrode and a working electrode disposed on the surface of said insulating needle member, a lead connected to said counter electrode, and a lead connected to said working electrode, wherein said lead connected to said working electrode is made of a linear conductive member which is finer than said needle member, said lead being partially embedded in said needle member and said conductive member protruding from the tip end of said needle member which protruding portion forms said working electrode.

2. The electrode probe in accordance with claim 1, further comprising a reagent layer formed on the surface of said needle member in contact with or in the vicinity of said electrode system.

3. The electrode probe in accordance with one 1, further comprising a third electrode and a lead connected thereto.

4. A body fluid examination equipment using the electrode probe in accordance with claim 1, comprising means for applying a voltage across the electrode system of said electrode probe and obtaining analyte information from said electrode system in the form of an electric signal, means for determining a measurement value of an analyte based on said electric signal and a body fluid leaking instrument.

5. The body fluid examination equipment in accordance with claim 4, further comprising display means for displaying a measurement value as determined.

6. An electrode probe comprising an insulating needle member, an electrode system including a counter electrode and a working electrode disposed on the surface of said insulating needle member, a lead connected to said counter electrode, and a lead connected to said working electrode, further comprising a pit formed at the tip end of said needle member, said pit being disposed with said working electrode and said counter electrode.

7. The electrode probe in accordance with claim 6, further comprising a reagent layer disposed in said pit.

8. The electrode probe in accordance with claim 6, further comprising a third electrode and a lead connected thereto.

9. A body fluid examination equipment using the electrode probe in accordance with claim 6, comprising means for applying a voltage across the electrode system of said electrode probe and obtaining analyte information from said electrode system in the form of an electric signal, means for determining a measurement value of an analyte based on said electric signal and a body fluid leaking instrument.

10. The body fluid examination equipment in accordance with claim 9, further comprising display means for displaying a measurement value as determined.

11. An electrode probe comprising an insulating needle member, an electrode system including a counter electrode and a working electrode disposed on the surface of said insulating needle member, a lead connected to said counter electrode, and a lead connected to said working electrode, wherein said lead connected to said working electrode is made of a linear conductive member which is finer than said needle member, said lead being partially embedded in said needle member and said conductive member being protruding inside a pit present at the tip end of said needle member, which protruding portion forms said working electrode.

12. The electrode probe in accordance with claim 11, further comprising a reagent layer disposed in said pit.

13. The electrode probe in accordance with claim 11, further comprising a third electrode and a lead connected thereto.

14. A body fluid examination equipment using the electrode probe in accordance with claim 11, comprising means for applying a voltage across the electrode system of said electrode probe and obtaining analyte information from said electrode system in the form of an electric signal, means for determining a measurement value of an analyte based on said electric signal and a body fluid leaking instrument.

15. The body fluid examination equipment in accordance with claim 14, further comprising display means for displaying a measurement value as determined.

16. An electrode probe comprising an insulating needle member having a pit at its tip end, an electrode system including a counter electrode and a working electrode disposed in said pit, a lead connected to said counter electrode and a lead connected to said working electrode.

17. The electrode probe in accordance with claim 16, further comprising a reagent layer disposed in said pit.

18. An electrode probe comprising an insulating needle member having a pit at its tip end, a counter electrode disposed in said pit, a lead connected to said counter electrode and a linear conductive member which is finer than said needle member, wherein said conductive member is partially embedded in said needle member and is protruding toward inside said pit of said needle member, which protruding portion serves as a working electrode.

19. The electrode probe in accordance with claim 18, further comprising a reagent layer disposed in said pit.

20. A body fluid examination equipment using an electrode probe comprising an insulating needle member, an electrode system including a counter electrode and a working electrode disposed on the surface of said insulating needle member, a lead connected to said counter electrode, and a lead connected to said working electrode, the equipment comprising means for applying a voltage across the electrode system of said electrode probe and obtaining analyte information from said electrode system in the form of an electric signal, means for determining a measurement value of an analyte based on said electric signal and a body fluid leaking instrument.

21. The body fluid examination equipment in accordance with claim 20 further comprising display means for displaying a measurement value as determined.

* * * * *